United States Patent
Murakoshi et al.

(10) Patent No.: US 6,762,428 B2
(45) Date of Patent: Jul. 13, 2004

(54) CREAM SOLDER INSPECTION METHOD AND APPARATUS THEREFOR

(75) Inventors: Takayuki Murakoshi, Kuwana-gun (JP); Makoto Tanaka, Nagoya (JP); Kazuo Ohashi, Kuwana-gun (JP)

(73) Assignee: Nagoya Electric Works Co. Ltd., Nagoya (JP)

( * ) Notice: Subject to any disclaimer, the term of this patent is extended or adjusted under 35 U.S.C. 154(b) by 196 days.

(21) Appl. No.: 09/904,458

(22) Filed: Jul. 16, 2001

(65) Prior Publication Data

US 2002/0005498 A1 Jan. 17, 2002

(30) Foreign Application Priority Data

Jul. 17, 2000 (JP) .................................. 2000-216070
Nov. 20, 2000 (JP) .................................. 2000-353007
Dec. 1, 2000 (JP) .................................. 2000-366856

(51) Int. Cl.$^7$ ............................................. G01N 21/86
(52) U.S. Cl. ................................. 250/559.34; 382/149
(58) Field of Search ................. 250/559.34, 559.19, 250/559.08, 559.2, 559.22, 559.12, 559.44, 559.46; 382/145–150; 356/601, 625, 237.4, 237.5; 348/125, 126, 92

(56) References Cited

U.S. PATENT DOCUMENTS

| | | | | |
|---|---|---|---|---|
| 5,943,125 | A | 8/1999 | King et al. | 356/237.1 |
| 5,949,901 | A | 9/1999 | Nichani et al. | 382/149 |
| 6,177,682 | B1 * | 1/2001 | Bartulovic et al. | 250/559.44 |
| 6,201,892 | B1 * | 3/2001 | Ludlow et al. | 382/149 |
| 6,525,331 | B1 * | 2/2003 | Ngoi et al. | 250/559.34 |

FOREIGN PATENT DOCUMENTS

JP          5-296746          11/1993

* cited by examiner

*Primary Examiner*—Thanh X. Luu
(74) *Attorney, Agent, or Firm*—Armstrong, Kratz, Quintos, Hanson & Brooks, LLP (57) ABSTRACT

An inspection method for cream solder for determining whether or not the shape of the cream solder is appropriate based on information on the height of the cream solder by irradiating light from substantially besides in two directions opposing each other through a lighting means to the cream solder so as to obtain at least two images and obtaining a difference between the obtained images.

26 Claims, 9 Drawing Sheets

CREAM SOLDER INSPECTION METHOD AND APPARATUS THEREFOR

BACKGROUND OF THE INVENTION

1. Field of the Invention

The present invention relates to a cream solder inspection method which inspects whether or not the cream solder coated preliminarily on a printed circuit board is applied in a proper condition to solder an electronic part on a printed circuit board and achieves a more secure inspection about the cream solder by removing a non-soldered portion which causes irregular reflection such as silk-printed portion, wiring pattern and bare pad located in the vicinity of that cream solder from an image photographed with a camera, and an inspection apparatus therefor.

2. Description of the Related Art

For example, Japanese Patent Application Laid-Open No. 5-29674 has disclosed a conventional cream solder inspection method. According to this method, light having a wave length of less than 600 nm is irradiated to the cream solder formed on an electrode made of copper foil on the print circuit board from obliquely above and then, reflection light, reflected from the aforementioned printed circuit board is allowed to enter into a camera located above so as to obtain a bright/dark image. Then, the quality of cream solder applying area is determined according to this bright/dark image.

According to the aforementioned publication, the quality of cream solder applying area is determined irrespective of presence/absence of a solder coating portion such as solder leveler or the quality of the cream solder is determined based on two-dimensional information so as to inspect the three-dimensional shape of the cream solder.

As for a method for coating the printed circuit board with the cream solder, a metallic screen containing small holes formed at its positions corresponding to cream solder applying positions is placed such that the aforementioned holes coincide with a cream solder printing face of the printing board and after that, the cream solder is applied to the printing face through the aforementioned holes in the screen. After the coating of the solder is finished, the screen is lifted up so that the printed cream solder is left at their applying positions through the holes in the screen. Then, the coating of the cream solder is completed.

Figure 4:
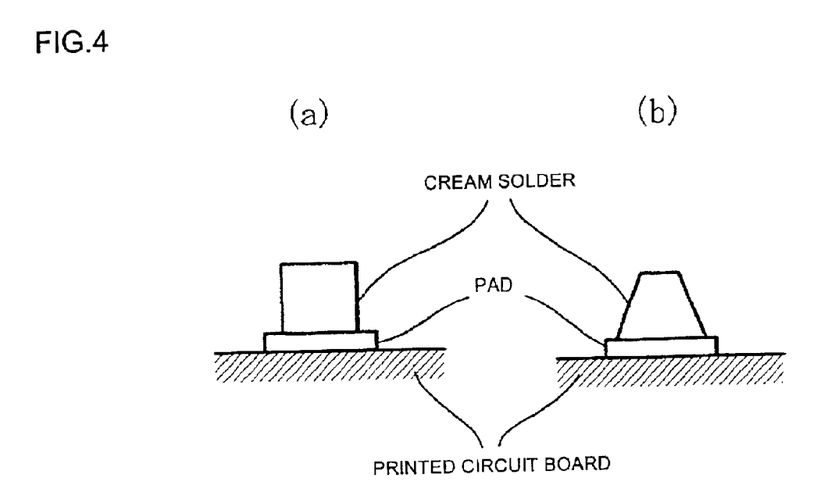
FIG. 4 is a side view showing proper and improper cream solders, while (a) indicates proper solder and (b) indicates improper solder.

Under such a coating method for the cream solder, when the aforementioned screen is lifted up, the cream solder, which is applied to such a small area of a soldering area as seen in recent years, is scraped from a peripheral face of its top portion by an inner peripheral face of each hole in the screen as shown in FIG. 4(b) as compared to a normal shape of the solder shown in FIG. 4(a), so that the amount of the solder becomes insufficient.

When the cream solder having such a configuration is inspected according to the technology disclosed in the aforementioned publication, that is, even in case of a printed circuit board having no solder coating portion like the solder leveler, it is impossible to detect that the cream solder is insufficient.

Further, if there is a portion having no solder, such as silk-printed portion, wiring pattern and bare pad, in the vicinity of an inspection place, that is, there is a non-soldered portion, the non-soldered portion, which causes reflection like the soldered portion, is mixed in the photographed image of the cream solder. Thus, the method for inspecting the shape of the cream solder has such a problem that accurate detection of the cream solder is disabled.

SUMMARY OF THE INVENTION

The present invention intends to solve the above described problem and therefore, an object of the invention is to provide an inspection method for cream solder capable of inspecting applying condition of the cream solder securely by irradiating light to the cream solder from at least two directions alternately, capturing that reflected light with a camera, obtaining a difference between the captured images to detect the shape of the cream solder and detect insufficiency of the cream solder and further removing a non-soldered portion printed in the vicinity of the cream solder, and an apparatus therefor.

To achieve the above object, according to an aspect of the present invention, there is provided an inspection method for cream solder for determining whether or not the shape of the cream solder is appropriate based on the information about the height of the cream solder by irradiating light from substantially besides in two directions opposing each other through a lighting means to the cream solder so as to obtain at least two images and obtaining a difference between the obtained images.

According to a preferred embodiment of the present invention, light is irradiated to the cream solder from substantially besides in at least two directions opposing each other alternately through a lighting means so as to obtain at least two images, a difference between the obtained images is calculated to obtain the information about the height of the cream solder and then, based on the information of the height whether or not the amount of the cream solder is appropriate is determined.

According to another aspect of the present invention, there is provided an inspection apparatus for the cream solder comprising: camera disposed above a printed circuit board which is subject of inspection; lighting means disposed substantially in the lateral direction of the cream solder applied to the printed circuit board and for irradiating light to the cream solder in two directions opposing each other alternately; arithmetic operating portion which switches the lighting means to get a difference between at least two images taken with the camera to obtain a side inclined portion of the cream solder from the luminance introduced from the difference; and determining portion for determining whether or not the shape of the cream solder is appropriate by comparing the value of the side inclined portion obtained by the arithmetic operating portion with a preliminarily set reference value.

According to still another aspect of the present invention, there is provided an inspection apparatus for the cream solder comprising: camera disposed above a printed circuit board which is subject of inspection; lighting means disposed substantially in the lateral direction of the cream solder applied to the printed circuit board and for irradiating light to the cream solder in two directions opposing each other alternately; image processing means for counting dimensions and area of an image of the solder taken with the camera; arithmetic operating means for computing the dimensions and area counted by the image processing means to obtain the amount of the solder; and control means provided with a program for inspecting the shape of the solder to control the respective means.

According to a further aspect of the present invention, there is provided an inspection apparatus for the cream solder comprising: camera disposed above the printed circuit board which is subject of inspection; lighting means disposed substantially in the lateral direction of non-soldered portion such as silk-printed portion formed on the printed circuit board and for irradiating light to the non-soldered portion in two directions opposing each other alternately; and arithmetic operating portion which switches the lighting means to obtain a difference between at least two images taken with the camera and removes the non-soldered portion from the image.

DESCRIPTION OF THE PREFERRED EMBODIMENTS

Hereinafter, a first embodiment of the cream solder inspection apparatus of the present invention will be described with reference to the accompanying drawings.

Figure 1:
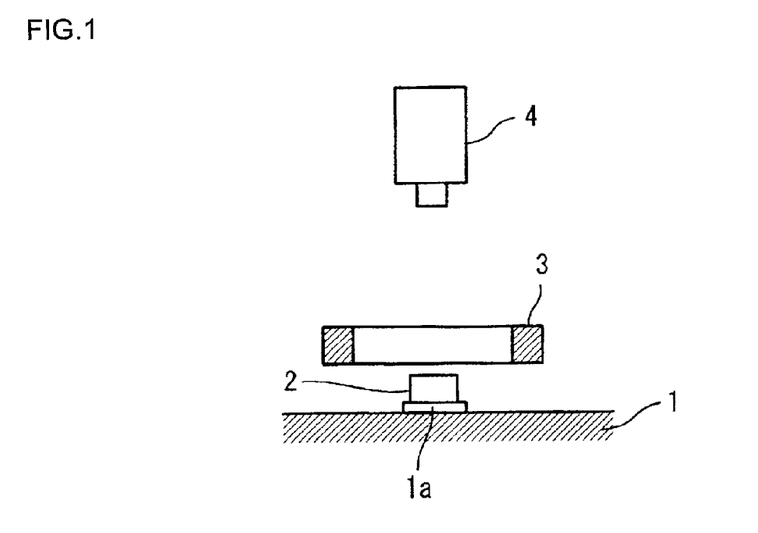
FIG. 1 is an explanatory diagram showing an allocation of a lighting means according to an embodiment of the cream solder inspection method of the present invention.

Referring to FIG. 1, reference numeral 1 denotes a printed circuit board and a pad 1a, which is conductive pattern, is formed on the printed circuit board 1 while cream solder 2 is applied on the pad 1a by screen printing as conventional. It is so constructed that the printed circuit board 1 is movable in the X-Y direction with a X-Y stage (not shown).

Reference numeral 3 denotes a lighting means fixed at a position apart from a top face of the aforementioned printed circuit board 1 by about 5-10 mm, in which a plurality of light sources such as LED are disposed such that they oppose each other so as to irradiate light substantially in a horizontal direction. The light sources disposed in the opposing state are divided by a switching circuit 6 which will be explained later so that a ring of the light sources is divided to four sections equal in width and only the light sources located at both ends turn on alternately.

Reference numeral 4 denotes a camera such as a video camera, which is fixed at a position apart from the top face of the printed circuit board 1 by about 100 mm. The lighting means 3 and said camera 4 are arranged in a fixed positional relationship with each other such that an optical axis of the camera 4 coincides with the center of the lighting means 3. Alternatively, said fixedly arranged lighting means 3 and the camera 4 may be adapted to bodily move in X-Y stage directions instead of the printed circuit board 1.

Next, a block diagram of FIG. 2 will be described. Similar reference numerals denote similar components and a description thereof is omitted.

Reference numeral 5 denotes an image memory for memorizing an image from the camera 4 and reference numeral 6 denotes a switching circuit for turning on the light sources opposing each other alternately in the lighting means 3. Each time when the lighting means 3 is switched by the switching circuit 6, the image memory 5 memorizes an image from the camera 4.

Reference numeral 7 denotes an arithmetic operating portion which obtains a difference of luminance between two images of the cream solder 2 when the light sources on both ends of the lighting means 3 are alternately turned on, said cream solder 2 is photographed under such illuminations to store the image of the thus photographed cream solder 2 in the image memory 5, and an area of a high luminance portion, length thereof or the like are calculated on the basis of information on the stored image of the cream solder 2. Reference numeral 8 denotes a determining portion which decides whether or not the shape of the cream solder 2 is normal by comparing a value from the arithmetic operating portion 7 with a predetermined reference value.

Next, an operation carried out under the abovementioned structure will be described.

Figure 3:
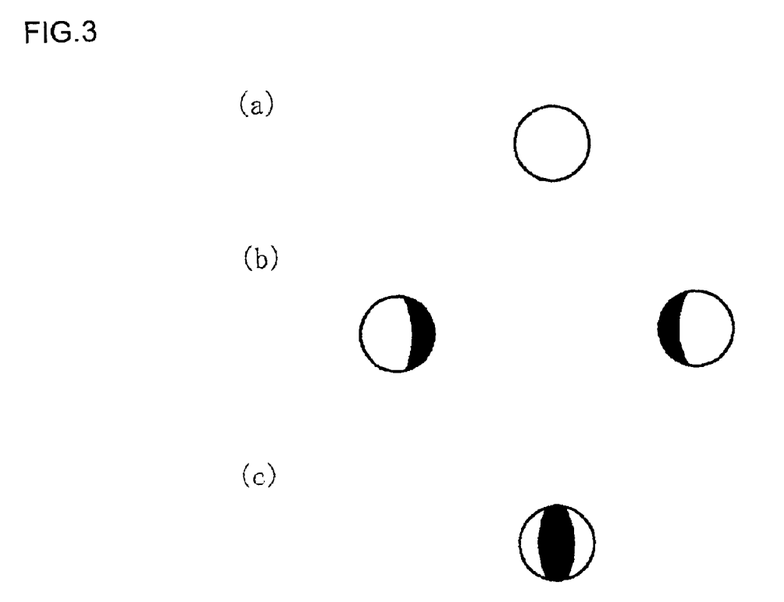
FIG. 3 shows an image taken with a camera while (a) is an image obtained when light is irradiated from above, (b) is an image obtained when light is irradiated from the right and left directions, and (c) is an image obtained according to a difference between two images.

First, FIG. 3 (a) shows an image taken with the camera 4 with all the light sources of the lighting means 3 turned on. When light is projected to the truncated cone cream solder 2 from substantially just beside and this condition is photographed with the camera 4 located just above, the shape of the cream solder 2 must be determined according to this information because the luminance of a side inclined portion of the cream solder is intensified. However, because the cream solder 2 is a particle of several tens microns and the top face thereof is not completely flat, it produces irregular reflection with light projected from substantially just beside, so that a difference of luminance between reflected light from the side face of the cream solder and the reflected light from the top face cannot be obtained sufficiently.

Therefore, according to the present invention, the light sources on both ends of the lighting means 3 are turned on alternately with the switching circuit 6, so that an image from the camera 4 is memorized in the image memory 5 each time when the lighting is switched (FIG. 3(b)). Next, if a difference between the aforementioned two images is obtained with the arithmetic operating portion 7, the top face, in which irregular reflection always occurs by lighting from both directions, is eliminated, so that an image, which has a high luminance on only its side inclined portions as shown in FIG. 3(c), is obtained.

The value of the inclined portion having a high luminance of this image is compared with the reference value set up preliminarily by the determining portion 8, for example, an area value. That is, if the area of the portion having a higher luminance is larger than the reference value, it means that the side inclined portion of the cream solder 2 is mildly inclined, thereby to indicate that the amount of solder is insufficient. Thus, as the reference values, the area and length of the inclined portion are set to determine what level of luminance is appropriate at a certain level of inclination and then, this reference value is used for the comparison and determination.

If the determining portion determines that the condition is defective, the fact that the shape of the cream solder 2 is defective is notified through one of various well-known methods.

In the above described embodiment, in an image obtained by switching the lighting means 3, there is a difference of the luminance between the cream solder 2 near the light source of the lighting means 3 and the cream solder 2 far therefrom because the luminance differs depending on the angle of optical axis from the light source. In this case, by making correction on the basis of the difference of the optical axis, it is possible to achieve more accurate determination.

Although in the above described embodiment, a case of employing the lighting means 3, in which LEDs are disposed in the form of a ring, has been exemplified, the similar cream solder appearance inspection may be carried out with a lighting means in which the LEDs are disposed in line.

Next, a shape inspection apparatus of a second embodiment will be described with reference to FIGS. 5-8.

Figure 5:
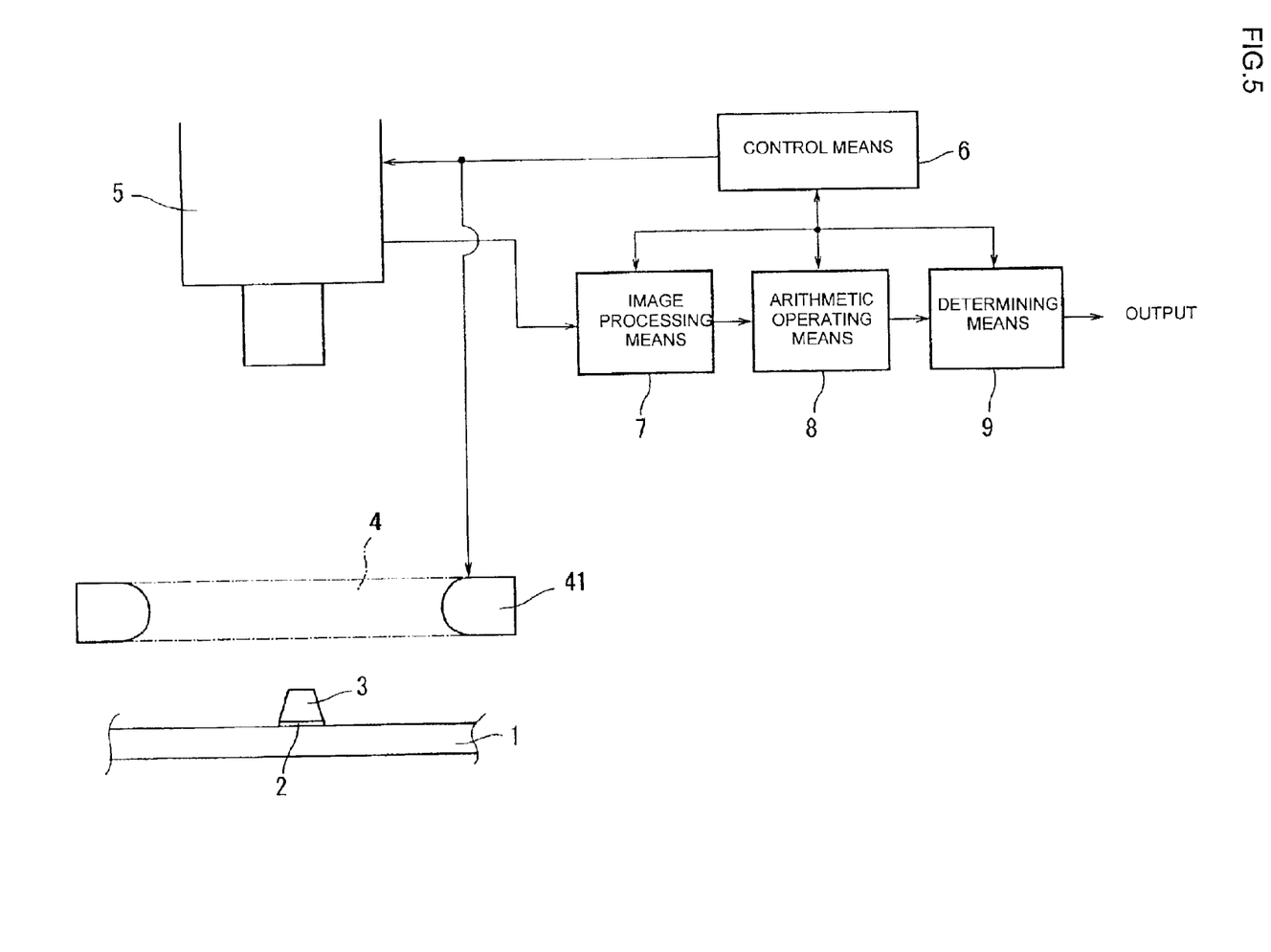
FIG. 5 is a block diagram showing a second embodiment.

Referring to FIG. 5, like reference numerals are attached to the same component as the first embodiment and a description thereof is omitted. In case where the cream solder 3 is BGA, it is shaped in a truncated cone whose top is missing as shown in the Figure. In case of cream solder for chip, it is a trapezoid having a rectangular bottom face and a top face such that the area of the top face is smaller than that of the bottom face.

Figure 13:
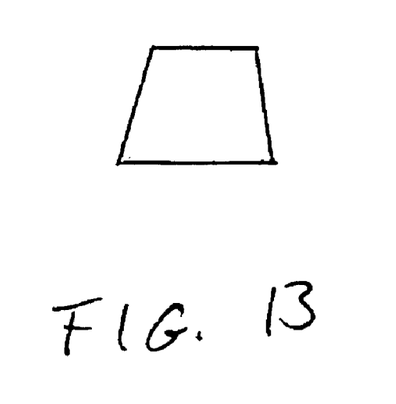
FIG. 13 is a schematic view of a truncated pyramid.

FIG. 13 shows the trapezoidal face of a truncated pyramidal shape of cream solder as seen in elevational view.

The reason why the top portion is smaller or in the truncated cone as shown in the Figure is that when a metal mask for use in printing is removed from the substrate, solder on the top end is absorbed by the mask so that it is removed. As the opening of the mask is decreased by employing finer pitch, that tendency is intensified.

Reference numeral 4 denotes a lighting means in which a plurality of LEDs (light emission diodes) 41 are disposed in the form of a ring such that they are directed to the center of its circle and this lighting means illuminates cream solder from a position very near the printed circuit board 1. The lighting means 4 is divided equally to four sections and the LEDs disposed so as to oppose as a result of dividing to four sections are turned on in succession. Reference numeral 5 denotes a camera for taking pictures of the cream solder 3 disposed on the printed circuit board 1 from above.

Referring to FIG. 5, reference numeral 6 denotes a control means loaded with a program for carrying out solder shape inspection. Reference numeral 7 denotes an image processing means for counting dimensions and area of solder from the image of solder taken with the camera 5. Reference numeral 8 denotes an arithmetic operating means for computing dimensions and area counted by the image processing means 7 so as to compute the amount of solder. Reference numeral 9 denotes a determining means for determining whether or not the amount of solder is proper by comparing with the reference solder amount preliminarily memorized in the control means 6.

Figure 7:
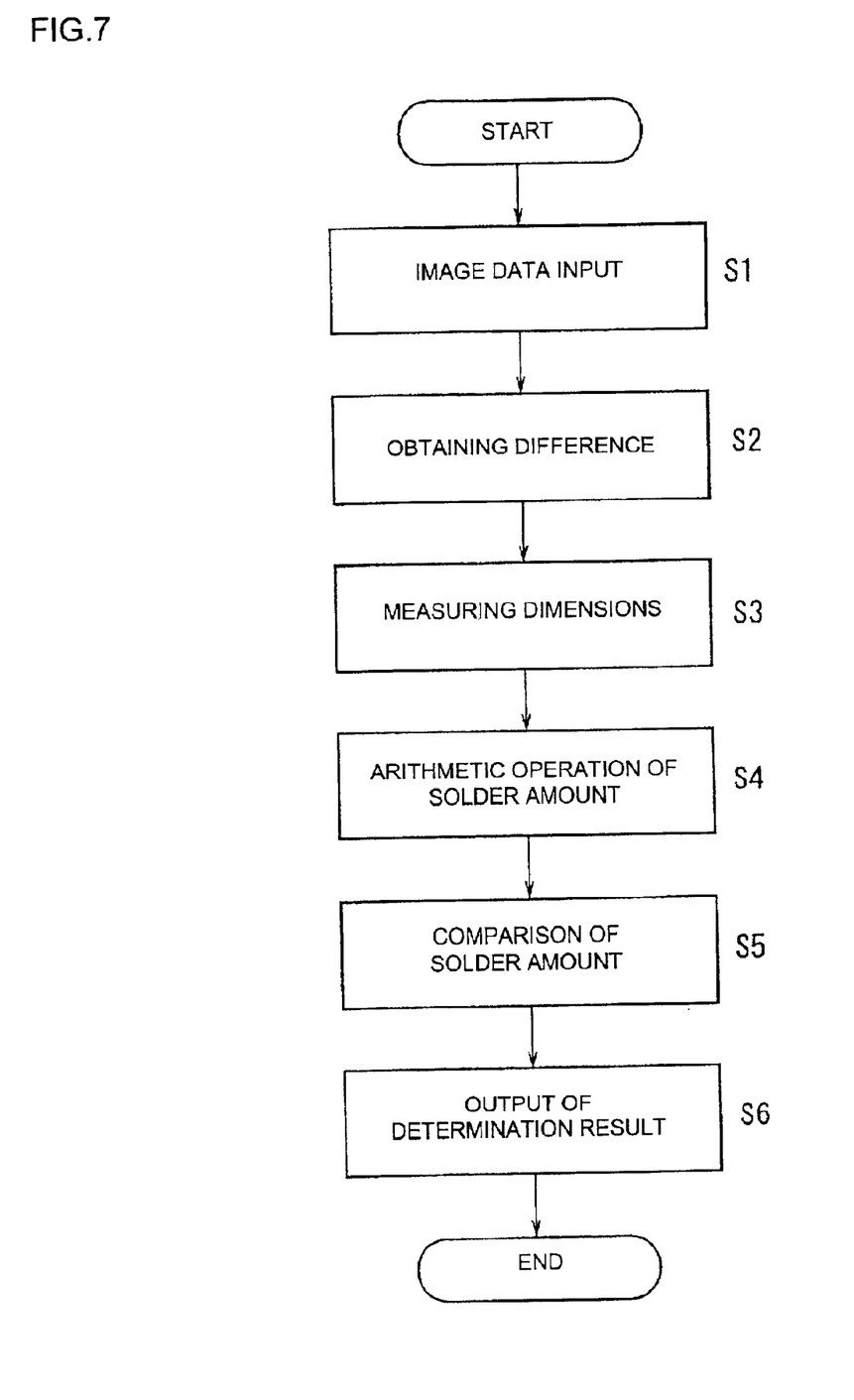
FIG. 7 is a flow chart showing a cream solder inspection method.

Next, the method for inspecting the amount of solder based on the aforementioned structure will be described with reference to a flow chart of FIG. 7.

In this flow chart, the operation will be described assuming that the printed circuit board 1 is carried into an inspection apparatus and the printed circuit board 1 is moved to a predetermined inspection position with the X-Y stage (not shown) so that a soldered portion, which is subject of inspection, is disposed below the camera 5.

Figure 6:
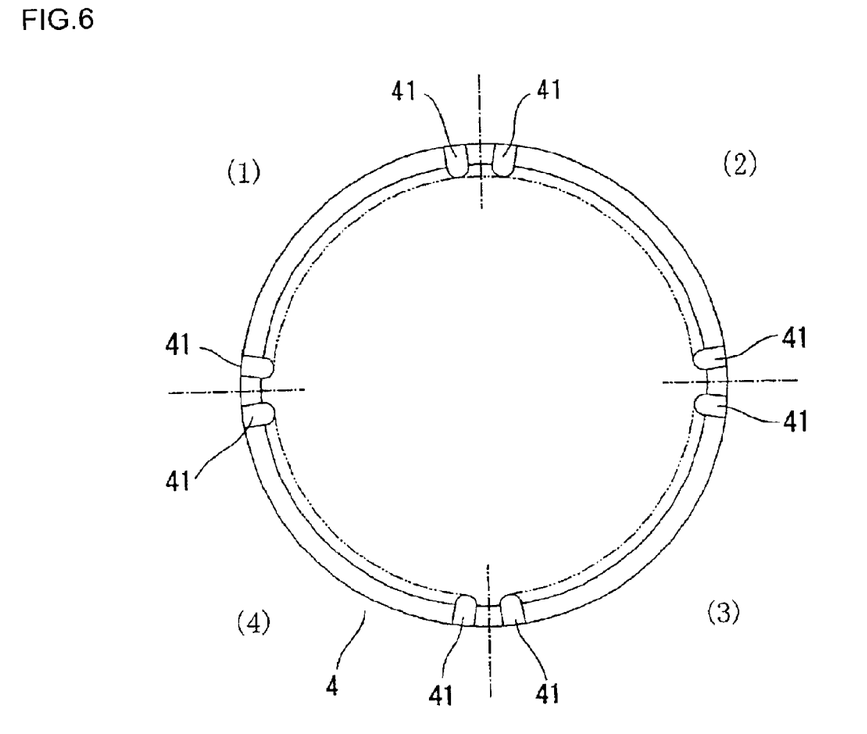
FIG. 6 is a plan view of a lighting means.

The lighting means 4 is turned on in the order of (1) (3), (2), (4) as shown in FIG. 6 to take pictures of each image and those images are memorized in a memory (not shown) of the control means 6 (step S1).

Figure 8:
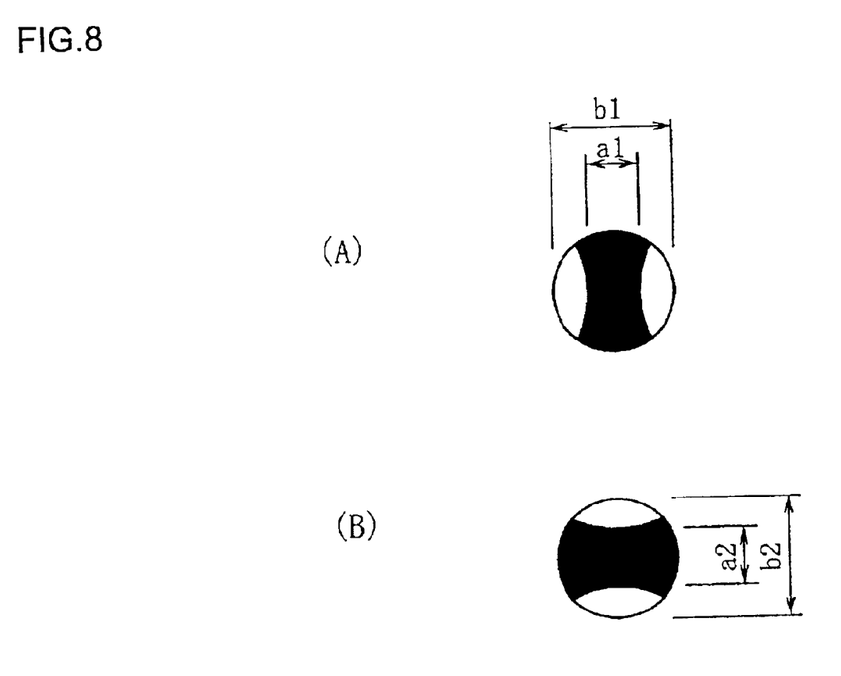
FIG. 8 is a differential image according to a difference obtained between images of a cream solder photographed by switching the light sources.

Next, by obtaining a difference between images taken when the lighting means (1), (3) and (2), (4) are turned on each to obtain differential images shown in FIGS. 8(A), (B) (step S2) Next, the differential images of FIG. 8 (A), (B) are processed to obtain an average diameter [(a1+a2)/2, (b1+b2)/2] between the top face and the bottom face from its edge components (step S3). (Where a1≅a2, b1≅b2) Next, the amount of solder V is calculated according to a following equation.

$$V = (h/3) \cdot \{Sa + \sqrt{(Sa \cdot Sb)} + Sb)\}$$

Here, h is the height of solder and Sa, Sb are areas of the top face and bottom face.

If this is expressed such that radius $\alpha \cong ((a1+a2)/2) \cdot \frac{1}{2}$, $\beta \cong ((b1+b2)/2) \cdot \frac{1}{2}$, it comes that $V \cong \pi \cdot h/3 \cdot (\alpha^2 + \alpha \cdot \beta + \beta^2)$.

Then, by substituting each diameter into the aforementioned equation, the amount of solder V is calculated (step S4). Finally, by comparing with the reference solder amount preliminarily memorized (step S5), a determination result is recorded or outputted (step S6).

Because h in the aforementioned equation is the thickness of metal mask, which is a known value, if it is intended to set up the reference solder amount VTH to be more than 70% the maximum value VMAX, it is permissible to obtain a value of $0.7 \cdot VMAX/\pi \cdot h/3$, memorize it in a reference table and then compare that result with a result of operation on an equation $(\alpha^2 + \alpha \cdot \beta + \beta^2)$ about only the radius.

Although in the above embodiment, a method in which solder is irradiated with one (a stage) illumination light source has been described, it is permissible to execute step illumination of illuminating from two directions (two stages) of from above and from beside, count the quantity of pixels contained in an edge of each of a top face and a bottom face of an image provided by obtaining a difference between those image data so as to obtain the aforementioned Sa, Sb directly and then execute the operation.

In case where the solder is shaped in a trapezoidal form such that it has rectangular bottom face and top face while that top face is smaller also, it is permissible to set up the lengths of sides of the top face and bottom face to be c1, d1 and c2, d2 by the aforementioned illumination so as to obtain those values and substitute them into an equation shown below to calculate the solder amount V.

$$V \cong (h/6) \cdot \{c1 \cdot d1 + (c1+c2) \cdot (d1+d2) + c2 \cdot d2\}$$

where a following approximate expression is established in case of $(c1 \cdot d1/c2 \cdot d2) \geq 0.7$.

$$V \cong (h/6) \cdot 2 \cdot (c1 \cdot d1 + c2 \cdot d2)$$

Thus, it is possible to determine whether or not the solder amount is appropriate from area of the top face and bottom face by counting the number of pixels. Therefore, after the area ratio is compared, inspection time can be shortened by executing the aforementioned simple arithmetic operation.

However, if only the area ratio is compared, it becomes more than 0.7 when the solder area on the bottom is small, thereby inducing an erroneous determination about whether or not the solder amount is appropriate. Thus, an accurate determination cannot be carried out until an actual solder amount is measured like the present invention.

As described above, the present invention intends to carry out approximate operation about the amount of cream solder in fine solder based on information about the area of solder on two-dimensional plane. As the methods for measuring the dimension of solder and its area, various well-known methods are available.

Next, a third embodiment will be described with reference to FIGS. 9–10. Like reference numerals are attached to the same components as the previously described embodiments and a description thereof is omitted.

Figure 9:
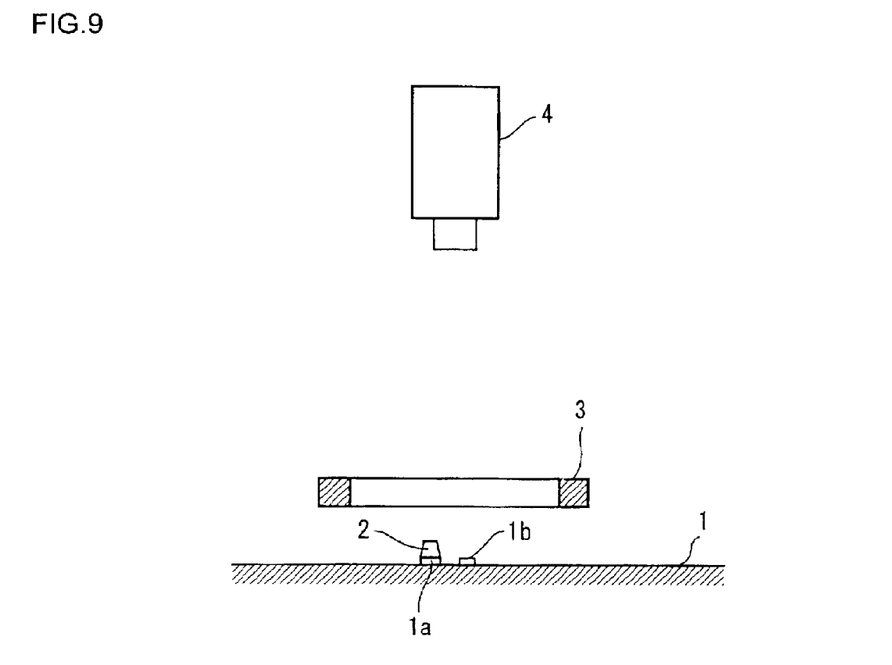
FIG. 9 is an explanatory diagram showing an outline of an apparatus according to a third embodiment.

Referring to FIG. 9, reference numeral 1b denotes a non-soldered portion which exists adjacent the pad 1a and is a portion having no solder there at such as silk-printed portion indicating a part number or the like, wiring pattern and bare pad. In FIG. 9, the pad 1a and the cream solder 2 are expressed in exaggerated fashion because pad 1a and cream solder 2 are actually so small as compared to the size of the lighting means that drafting thereof on the same paper at the same scale are impossible. This is the case with FIG. 1 and FIG. 5.

Figure 2:
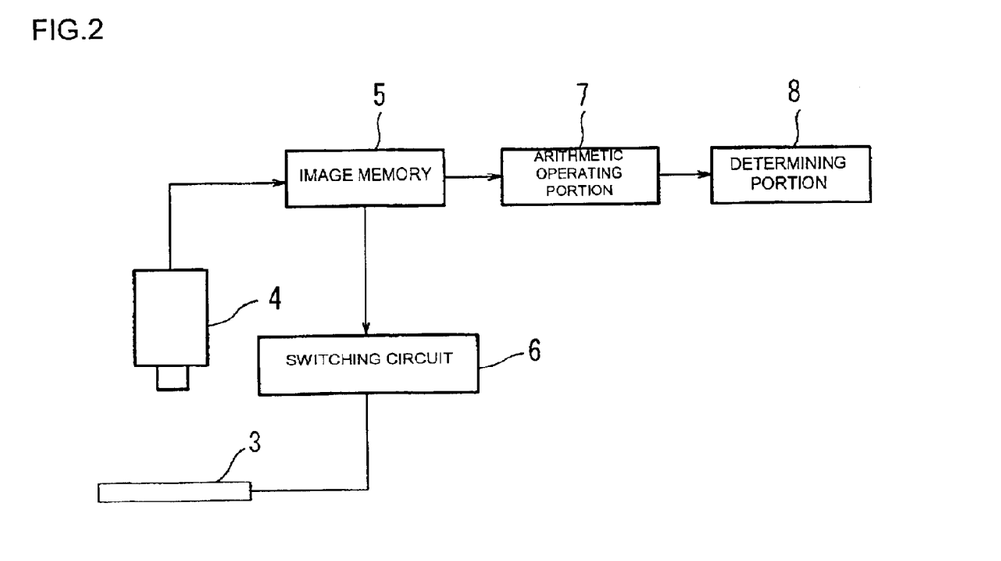
FIG. 2 is a block diagram of the same inspection apparatus.

Meanwhile, because this embodiment has the same structure as FIG. 2 of the first embodiment described previously, a description of the block diagram is omitted. Then, an operation of this embodiment will be explained based on the block diagram of FIG. 2.

First, the light sources of the lighting means 3 are turned on alternately by means of the switching circuit 6 and each time of that lighting means switching, an image from the camera 4 is memorized alternately into the image memory 5. Next, by obtaining a difference between the aforementioned two images in the arithmetic operating portion 7, the non-soldering portion 1b in which irregular reflection occurs by lighting from both sides is eliminated and removed from the image.

Thus, in case of inspection of the shape of the cream solder 2, the non-soldered portion 1b is removed from the image so that an image of only the cream solder 2 is provided. Therefore, it is possible to omit a procedure for inputting position data of the non-soldered portion 1b and then removing it from a taken picture without affecting the inspection of the shape of the cream solder 2.

Next, an operation for carrying out the inspection of the shape of the cream solder by removing the non-soldered portion 1b from the screen will be described with reference to FIG. 10.

Figure 10:
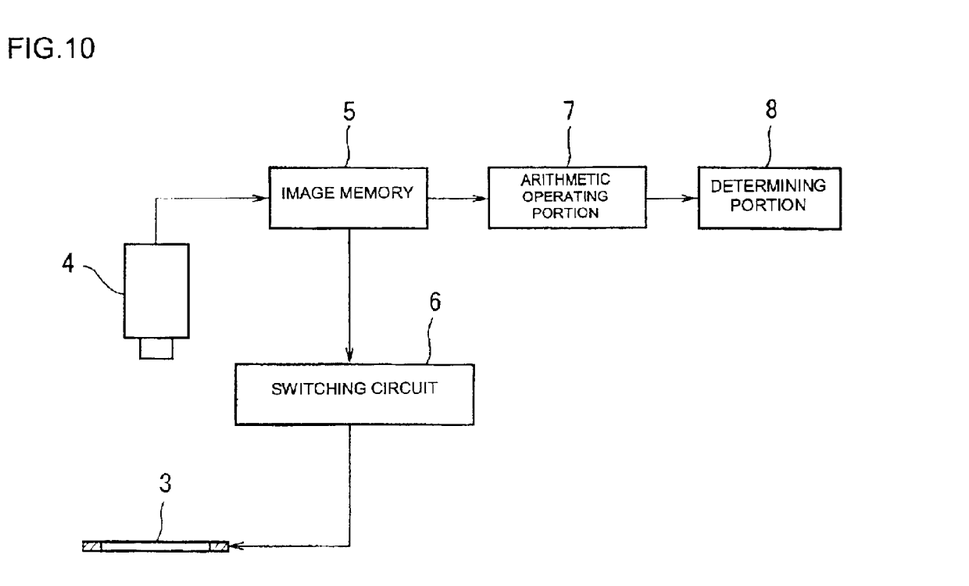
FIG. 10 is a block diagram showing the same apparatus.

First of all, the light sources of the lighting means 3 are turned on alternately by means of the switching circuit 6 and each time of such switching of the light sources, an image from the camera 4 is memorized in the image memory 5 (FIG. 10(a)). Next, by obtaining a difference between the two images in the arithmetic operating portion 7, the non-soldered portion 1b in which irregular reflection occurs by lighting from both sides and the top face portion of the cream solder 2 are eliminated so that an image shown in FIG. 10 (b), in which only the side inclined portion has a high luminance, is obtained.

Therefore, the non-soldered portion 1b is removed from the image, so that the inspection of the shape of the cream solder 2 can be executed without considering the non-soldered portion 1b. Therefore, only the inclined portion of the cream solder 2 having a high luminance exists in this image and thus, the value of that inclined portion is compared with the reference value set up in the determining portion 8, for example, area value thereof.

That is, a fact that area of a portion having a high luminance is larger than the reference value means that the side inclined portion of the cream solder 2 is mildly inclined, indicating that the solder amount is insufficient. Therefore, the area value and length of the inclined portion for determining that the luminance at a certain inclination is proper are set up as a reference value and then the determination is carried out by comparing with this reference value.

Then, if the determining portion 8 decides that the shape of solder is defective, a fact that the shape of the solder 2 is defective is notified according to various well-known methods.

According to the previously-described embodiment, in an image obtained by switching the lighting means 3, the non-soldering portion 1b and the cream solder 2 near the light source of the lighting means 3 have a different angle of optical axis from the light source than the non-soldering portion 1b and the cream solder 2 far therefrom, so that the luminance is different. Thus, by correcting following the difference of the optical axis, the non-soldered portion 1b is removed completely and by inspecting the shape of the cream solder 2, whether or not the solder amount is appropriate can be determined accurately.

Figure 11:
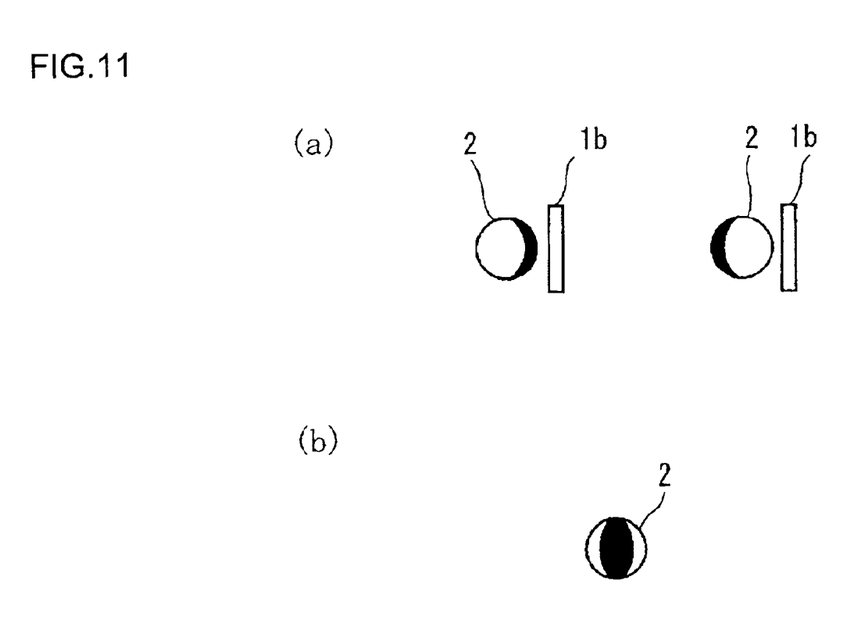
FIG. 11 is an image taken with a camera, while (a) is an image obtained when light is irradiated from the right and left directions and (b) is an image obtained according to a difference between two images.
Figure 12:
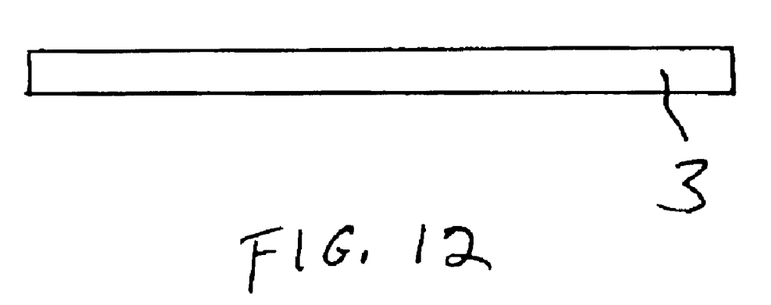
FIG. 12 is a schematic view of lights deployed in a line shape.

Although in the above described embodiment, the method of using the lighting means 3 in which the LEDSs are disposed in the form of a ring has been exemplified, a lighting means in which the LEDs are disposed in line as in FIG. 11(a), FIG. 11(b), and FIG. 12, showing a lighting means 3 in line shape, is also capable of inspecting eh shape of the cream solder with the non-soldering portions 1b removed like the previously-described cases.

Although the aforementioned bare pad means a pad in which the cream solder is not printed for the purpose of design, in case of a pad which should be printed with the cream solder properly but is turned to a bare pad because of printing failure, all or part of data in that inspection portion is removed, so that whether the shape of the cream solder is appropriate can be determined.

According to the present invention, as described above, light is irradiated to the creams solder from substantially besides in at least two directions opposing each other alternately through a lighting means so as to obtain at least two images, a difference between those images is calculated to obtain information about the height of the cream solder and then, whether or not the shape of the cream solder is appropriate is determined. Thus, when the top portion of the cream solder is scraped in process of screen-printing, it is possible to detect and determine that that condition is improper.

Luminance of reflected light from the cream solder at a low place is classified to plural grades of high, medium and low, for example and then, by finding which grade the luminance introduced from the obtained difference belongs to, whether or not the shape of the cream solder is appropriate is determined. As a result, it is possible to setup the criterion for determining whether the shape of the cream solder is acceptable freely.

Further, light is irradiated to the cream solder from substantially besides in at least two directions opposing each other alternately through the lighting means so as to obtain at least two images, a difference between those image is obtained to obtain information about the height of the cream solder and whether or not the amount of the cream solder is appropriate is determined based on the information about the height thereof. As a result, the amount (volume) of such a minute cream solder can be obtained simply and easily. Thus, by comparing the amount of the cream solder obtained in this manner with a reference solder amount preliminarily memorized, whether or not the shape of the cream solder is appropriate can be determined quickly and accurately.

Further, light is irradiated to the non-soldered portion such as a silk-printed portion formed on a printed circuit board alternately with the lighting means, the reflected light from the non-soldered portion is photographed with the camera and a difference between at least the two bright/dark images is obtained to remove the non-soldered portion from the image. Consequently, the image of the non-soldered portion is removed from the image fetched in with the camera upon inspection of the quality of the cream solder. Thus, that inspection on the quality of the cream solder can be executed without considering the non-soldered portion. Therefore, there is such an effect that the inspection can be carried out accurately and simply.

What is claimed is:

1. An inspection method for cream solder for determining whether or not the shape of the cream solder applied on a printed circuit board is appropriate based on information about a side inclined portion of the cream solder, the method comprising irradiating the cream solder with light alternately from at least two illumination directions opposing each other in a single plane extending substantially parallel to the printed circuit board in close proximity thereto, said irradiated light hitting the cream solder, each of the illumination directions being substantially perpendicular to a viewing direction;

obtaining images along the viewing direction, the images being corresponding to respective irradiations in the illumination directions; and obtaining a difference between the obtained images.

2. An inspection method for the cream solder according to claim 1, wherein the steps of obtaining at least two images, further comprising bright/dark images, and obtaining a difference further comprising taking pictures of a reflection light from the cream solder with a camera disposed above, obtaining a difference between at least two of the bright/dark images so as to determine the inclination of the side inclined portion of the cream solder from a luminance of the inclined portion, and comparing a value of the luminance of the side inclined portion with a reference value set up preliminarily for determining whether or not the shape of the cream solder is appropriate.

3. An inspection method for the cream solder according to claim 1, wherein the solder is shaped generally as truncated cones or generally as truncated pyramids and is printed on a substrate, and wherein the method comprises photographing the solder with a camera disposed above the substrate, calculating information about areas of a top face and a bottom face of the solder from an image of the photographed solder and computing an amount of the solder from the areas by an arithmetic operation.

4. An inspection method for the cream solder according to claim 1, further including calculating a difference between the obtained images to gain information about the side inclined portion of the cream solder and then determining whether or not a shape of the cream solder is appropriate, photographing with a camera light reflected from a non-soldered portion of the printed circuit board to obtain at least two images and then obtaining a difference between at least two bright/dark images to remove the non-soldered portion from the difference between the obtained two images.

5. The inspection method according to claim 1, wherein the step of irradiating the cream solder alternately with light from at least two illumination directions opposing each other further comprises illuminating from lights deployed in line-shapes or illuminating from segments of lights deployed in a ring-shape.

6. The inspection method according to claim 5, wherein the segments of lights deployed in a ring-shape comprise four segments in an LED ring.

7. The inspection method according to claim 1, wherein the cream solder is printed on a substrate, and wherein each of the illumination directions is a direction from 5–10 mm elevation above the substrate.

8. The inspection method according to claim 1, wherein the cream solder is shaped generally as truncated cones or generally as truncated pyramids including the side inclined portion.

9. An inspection method for cream solder wherein the solder applied on a printed circuit board is shaped generally as truncated cones or generally as truncated pyramids, comprising steps of irradiating light onto each cone or pyramid alternately from at least two illumination directions opposing each other in a single plane extending substantially parallel to the printed circuit board in close proximity thereto, through a lighting means, said irradiated light hitting the cream solder so as to obtain at least two images, each of the illumination directions being substantially perpendicular to a viewing direction;

calculating a difference between the two images to gain information about a side inclined portion of the cream solder and then determining whether or not the shape of the cream solder is appropriate based on the information about the side inclined portion.

10. An inspection method for the cream solder according to claim 9 wherein a reflection light from a non-soldered portion of the printed circuit board is photographed with a camera and then a difference between at least two bright/dark images is obtained to remove the non-soldered portion from the image.

11. The inspection method according to claim 9, wherein the step of irradiating the cream solder alternately with light from at least two illumination directions opposing each other further comprises illuminating from lights deployed in line-shapes or illuminating from segments of lights deployed in a ring-shape.

12. The inspection method according to claim 11, wherein the segments of lights deployed in a ring-shape comprise four segments in an LED ring.

13. The inspection method according to claim 9, wherein the cream solder is printed on a substrate, and wherein each of the illumination directions is a direction from 5–10 mm elevation above the substrate.

14. An inspection apparatus for a cream solder on a printed circuit board, the apparatus comprising:

a camera disposed above the printed circuit board which is subject to inspection;

a lighting means disposed to irradiate substantially in a lateral direction relative to the cream solder applied to the printed circuit board and for irradiating light onto the cream solder alternately in two directions opposing each other in a single plane extending substantially parallel to the printed circuit board in close proximity thereto;

an arithmetic operating portion which obtains a difference of luminance between at least two images of a side inclined portion of the cream solder photographed with said camera by alternately turning on the lighting means; and a determining portion for deciding whether or not the shape of the cream solder is appropriate by comparing a luminance of a the side inclined portion of the solder obtained by the arithmetic operating portion with a preliminarily set reference value.

15. The apparatus according to claim 14, wherein the lighting means further comprises lights deployed in line-shapes or segments of lights deployed in a ring-shape.

16. The apparatus according to claim 15, wherein the segments of lights deployed in a ring-shape comprise four segments in an LED ring.

17. The apparatus according to claim 14, wherein each of the two directions is a direction from 5–10 mm elevation above the printed circuit board.

18. An inspection apparatus for a cream solder on a printed circuit board, the apparatus comprising:

a camera disposed above the printed circuit board which is subject to inspection;

a lighting means disposed to irradiate substantially in a lateral direction relative to the cream solder applied to the printed circuit board and for irradiating light onto the cream solder alternately in two directions opposing each other in a single plane extending substantially parallel to the printed circuit board in close proximity thereto;

image processing means for determining dimensions and area of the solder from an image of the solder taken with the camera;

arithmetic operating means for computing an amount of solder from the dimensions and area determined by the image processing mean; and control means provided with a program for inspecting a shape of the solder to control the apparatus.

19. The apparatus according to claim 18, wherein the lighting means further comprises lights deployed in line-shapes or segments of lights deployed in a ring-shape.

20. The apparatus according to claim 19, wherein the segments of lights deployed in a ring-shape comprise four segments in an LED ring.

21. The apparatus according to claim 18, wherein each of the two directions is a direction from 5–10 mm elevation above the printed circuit board.

22. The apparatus according to claim 18, wherein the cream solder is shaped generally as a truncated cone or generally as a truncated pyramid including the side inclined portion.

23. An inspection apparatus for a cream solder on a printed circuit board, the apparatus comprising:

a camera disposed above the printed circuit board which is subject to inspection;

a lighting means disposed to irradiate substantially in a lateral direction of a non-soldered portion formed on the printed circuit board and for irradiating light onto the non-soldered portion alternately in two directions opposing each other alternately in a single plane extending substantially parallel to the printed circuit board in close proximity thereto; and an arithmetic operating portion which switches the lighting means to obtain a difference between at least two images taken with the camera and removes the non-soldered portion from the image.

24. The apparatus according to claim 23, wherein the lighting means further comprises lights deployed in line-shapes or segments of lights deployed in a ring-shape.

25. The apparatus according to claim 24, wherein the segments of lights deployed in a ring-shape comprise four segments in an LED ring.

26. The apparatus according to claim 23, wherein each of the two directions is a direction from 5–10 mm elevation above the printed circuit board.

* * * * *